United States Patent
Gavaris

(10) Patent No.: US 10,286,035 B2
(45) Date of Patent: May 14, 2019

(54) OPHTHALMIC TREATMENT COMPOSITION AND VEHICLE FOR DELIVERY OF PHARMACEUTICAL SUBSTANCES OR THERAPEUTIC AGENTS

(71) Applicant: Paul Gavaris, Bethesda, MD (US)

(72) Inventor: Paul Gavaris, Bethesda, MD (US)

(*) Notice: Subject to any disclaimer, the term of this patent is extended or adjusted under 35 U.S.C. 154(b) by 0 days.

(21) Appl. No.: 15/292,718

(22) Filed: Oct. 13, 2016

(65) Prior Publication Data
US 2017/0128522 A1    May 11, 2017

Related U.S. Application Data

(60) Provisional application No. 62/241,462, filed on Oct. 14, 2015.

(51) Int. Cl.
| | |
|---|---|
| *A61K 9/00* | (2006.01) |
| *A61K 9/08* | (2006.01) |
| *A61K 31/01* | (2006.01) |
| *A61K 38/13* | (2006.01) |
| *A61K 47/06* | (2006.01) |
| *A61K 31/496* | (2006.01) |
| *A61K 31/573* | (2006.01) |
| *A61K 31/7048* | (2006.01) |

(52) U.S. Cl.
CPC ............ *A61K 38/13* (2013.01); *A61K 9/0048* (2013.01); *A61K 9/08* (2013.01); *A61K 31/01* (2013.01); *A61K 31/496* (2013.01); *A61K 31/573* (2013.01); *A61K 31/7048* (2013.01); *A61K 47/06* (2013.01)

(58) Field of Classification Search
CPC ................ A61K 31/496; A61K 31/573; A61K 31/7048; A61K 38/13; A61K 31/01; A61K 47/06; A61K 9/0048; A61K 9/08
See application file for complete search history.

(56) References Cited

U.S. PATENT DOCUMENTS

| | | | |
|---|---|---|---|
| 3,821,375 A | 6/1974 | Alper | |
| 5,474,979 A | 12/1995 | Ding et al. | |
| 8,629,111 B2 | 1/2014 | Acheampong et al. | |
| 8,633,162 B2 | 1/2014 | Acheampong et al. | |
| 8,685,930 B2 | 1/2014 | Acheampong et al. | |
| 8,642,556 B2 | 2/2014 | Acheampong et al. | |
| 8,648,048 B2 | 2/2014 | Acheampong et al. | |
| 9,119,772 B2 | 9/2015 | Trogden et al. | |
| 9,248,191 B2 | 2/2016 | Acheampong et al. | |
| 2006/0148686 A1 | 7/2006 | Xia et al. | |
| 2007/0265353 A1 | 11/2007 | Matsuhisa | |
| 2008/0299206 A1 | 12/2008 | Lee et al. | |
| 2010/0016264 A1 | 1/2010 | Connor et al. | |
| 2010/0160293 A1 | 6/2010 | Tojo et al. | |
| 2010/0323978 A1* | 12/2010 | Hanna ................ | A61K 9/0048 514/29 |
| 2012/0190661 A1 | 7/2012 | Trogden | |
| 2013/0345150 A1 | 12/2013 | Steele | |
| 2014/0141106 A1 | 5/2014 | Gore et al. | |
| 2014/0274985 A1 | 9/2014 | Malhotra et al. | |
| 2015/0174211 A1 | 6/2015 | Nanduri et al. | |

OTHER PUBLICATIONS

Allergan Inc., Restasis® cyclosporine eye drop product specification, 2009, pp. 1-8 (Year: 2009).*
Safety Assessment Panel (Final Report on the Safety Assessment of squalane and squalene, Int. J. Toxicology, 1990, vol. 1, pp. 37-56) (Year: 1990).*

* cited by examiner

*Primary Examiner* — Kortney L. Klinkel
(74) *Attorney, Agent, or Firm* — R. Neil Sudol; Henry D. Coleman

(57) ABSTRACT

An ophthalmic treatment composition for the treatment of dry eye consists essentially of squalane in an amount by weight of 1% to 100%; and mineral oil in an amount by weight of 0% to 99%. Preferably, the mineral oil is a light mineral oil or mixture of light mineral oils and is present in an amount by weight of 1% to 10%. The composition is effectively devoid of water, preservatives, emulsifiers and dispersing agents. A related ophthalmic treatment composition comprises squalane in an amount by weight of 1% to 99% and mineral oil in an amount by weight of 0% to 99% and at least one hydrophobic or lipophilic pharmaceutical substance in an amount by weight of 0.01% to 5%, effective for treatment of at least one ophthalmic condition.

13 Claims, No Drawings

OPHTHALMIC TREATMENT COMPOSITION AND VEHICLE FOR DELIVERY OF PHARMACEUTICAL SUBSTANCES OR THERAPEUTIC AGENTS

BACKGROUND OF THE INVENTION

This invention relates to a composition and associated method for treatment of certain ophthalmic conditions. The invention also relates to a composition and associated method for treatment of a number of disease states via an ophthalmic delivery process. The invention further relates to a composition for use as a delivery vehicle or carrier in the manufacture of a composition containing a pharmaceutical substance or therapeutic agent.

Dry eye syndrome is characterized by sensations of dryness, burning, and a sandiness or grittiness that can worsen during the day. Symptoms are typically described as burning, itchy, scratchy, stingy or tired eyes. Other symptoms include pain, redness, a pulling sensation, and pressure behind the eye. The damage to the eye surface resulting from dry eye increases discomfort and sensitivity to bright light and both eyes usually are affected, but symptoms may be occur asymmetrically.

Having dry eyes for a prolonged period of time can lead to tiny abrasions on the surface of the eyes. In advanced cases, the epithelium undergoes pathologic changes, namely squamous metaplasia and loss of goblet cells sometimes due to activation of T cells directed. Some severe cases result in thickening of the corneal surface, corneal erosion, punctate keratopathy, epithelial defects, corneal ulceration, corneal neovascularization, corneal scarring, corneal thinning, and even corneal perforation. An abnormality of any one of the three layers of tears which produces an unstable tear film, may result in symptoms of keratitis sicca.

Another significant benefit of this invention is to provide a preservative-free vehicle for ophthalmic medications. With such chronic conditions as glaucoma, allergies, uveitis, and dry eye and with other frequent needs, the use of ophthalmic medications containing preservatives is counter-productive as they often produce serious side effects to the eye and adnexal structures and accordingly should to be stopped. The preservatives being surfactants damage the epithelium with each use in an infected or already allergic conjunctiva thus reducing the full effectiveness of the desired therapy. Therefore this invention affords significant benefit on 2 major venues, namely, it eliminates the deleterious effects of preservatives, and by its inherent therapeutic antioxidant and emollient properties supplements the therapeutic goal. Another benefit of the present invention is that the medications can be delivered in a single daily dose at night, easily in a dropper bottle form that patients find convenient and economical in lieu of the single-use plastic dropperettes that can scratch the corneas.

There is a need for an improved method and composition for the treatment of chronic ophthalmic conditions such as dry eye (DED) and glaucoma. Conventional treatments require frequent use of eye drops instilled into the eye. There is a high level of interest in using food oils, such as olive oil, in ocular formulas for dry eye treatment or other chronic ophthalmic diseases. Compositions have been proposed which include castor oil to facilitate spreading of the composition over the surface of the eye. See, e.g., U.S. Patent Application Publication No. 2008/0070834 and U.S. Pat. No. 8,679,554.

The great majority of the compositions used include either a preservative such as polysorbate 80 (U.S. Pat. No. 8,679,554), benzalconium chloride or thimerosal and/or an emulsifier or surfactant (Publication No. 2008/0070834). The preservatives and emulsifiers are either toxic to the epithilial cells or are allergenic to the patients. Over time this mild toxicity when induced 2-3 times a day can create serious redness, tissue changes such as conjunctival contracture or subconjunctival fibrosis, and actual damage to already compromised tissue. Thus any method of drug delivery which does not contain these preservatives would be much preferred and would be ready substitutes for present vehicles for eye drug delivery or have inherent emollient benefits as well.

OBJECTS OF THE INVENTION

It is an object of the present invention to provide an improved composition for the treatment of dry eye, the composition serving either as a medication delivery vehicle and/or as an emollient.

A more specific object of the present invention is to provide a composition for the treatment of dry eye which does not include even incidental amounts of preservatives and emulsifying agents.

A related object of the present invention is to provide an improved vehicle for delivering a therapeutic agent primarily to the corneal epithelium and adnexal structures.

An associated specific object of the invention is to provide a medicament delivery vehicle or composition which does not include even incidental amounts of preservatives and emulsifying agents.

These and other objects of the invention will be apparent from the descriptions herein. Although every object of the invention is attained in at least one embodiment of the invention, there is not necessarily any embodiment which attains all of the objects of the invention.

SUMMARY OF THE INVENTION

The present invention is directed to a composition for use in the treatment of undesirable ophthalmic conditions including dry eye and various disease states such as allergic conjunctivitis, atopic dermatitis, or eczematous change, or as a protective from excess tears. The composition comprises 100% squalane alone or optionally in combination with mineral oil, preferably a light mineral oil (N.F.). It is contemplated that the composition is essentially devoid of preservatives, emulsifiers and surfactants. Impurities may be incidentally present in the composition but only in trace amounts that have no practical, cognizable or determinable effect on the properties of the composition or its effect on human users. The composition is typically used via topical application to the eye of a mammal, suffering from dry eye, to relieve the symptoms thereof via its several properties such as its emollient properties or its inherent pharmaco-therapeutic actions.

Furthermore, the present invention contemplates a method for treating keratoconjunctivitis sicca (KCS) or dry eye comprising providing the above composition, and administering said composition topically to the ocular surface or immediate vicinity of an eye of a patient. This ophthalmic treatment composition is hypo-allergenic and of virtually zero toxicity to ophthalmic tissues.

Moreover, such a dry-eye treatment composition may be used as a delivery vehicle or carrier composition for a wide array of ophthalmic medicaments and pharmaceuticals, including but not limited to cyclosporin, prostaglandins, hydrocortizone, prednisone, prednisolone, dexamethasone, hydrophobic antibiotics, hydrophobic anti-inflammatories, hydrophobic antihistamines, hydrophobic NSAIDs, hydrophobic hormones such as estrogen, progesterone, and testosterone. Accordingly, the dry-eye treatment composition is useful as a delivery vehicle or carrier component in the manufacture of a medicament to be applied to the eye directly or indirectly via the eyelid, where the medicament includes a pharmaceutical substance or therapeutic agent in addition to the delivery vehicle or carrier. The light mineral oil is provided in an amount which enables effective solubility of the pharmaceutical component whether one or more of the exemplary therapeutic agents identified herein or any other suitable agent, medicament, or pharmaceutical substance.

Squalane is a hydrocarbon and triterpene derived by hydrogenation of squalene. Due to the complete saturation of squalane, it is not subject to auto-oxidation. The name selected for squalane by the International Union of Pure and Applied Chemistry (IUPAC) is 2,6,10,15,19,23-Hexamethyltetracosane. Squalane may be obtained from shark liver or olive oil, the latter route being preferred.

Ophthalmic treatment compositions according to the present invention have a soothing and healing effect on the eye. In the case of dry eye, the composition reduces or eliminates characteristic symptoms of dryness, burning, sandiness or grittiness, itchiness, stinging, tiredness, pain, redness, pulling sensations, pressure sensations and sensitivity to bright light or pain.

A dry-eye treatment composition or a drug delivery vehicle composition in accordance with the present invention is clear, without odor, non-allergenic or at least minimally allergenic to extremely sensitive patients. It has a soothing or comforting effect on even undiagnosed ocular conditions. The present composition is hydrophobic and therefore able to dissolve medicinal molecules such as cyclosporin and other oil soluble medicaments. The composition has a hygroscopic chemistry that naturally inhibits bacterial growth, similar to olive oil or 100% glycerin, both of which have been left open or in a container without needing a preservative to maintain sterility. The compositions according to the present invention are therefore storage stable at room temperatures.

A composition in accordance with the present invention has very high antioxidant, therapeutic and emollient properties. It may include light mineral oil, N.F., in any percentage as a diluent and solubility enhancing component to any degree, i.e. from 1% vol. per vol. to 99% vol./vol. and still retain its basic self preserving properties. The light mineral oil, N.F. (national formula), is included in a delivery vehicle or carrier composition as needed in order to provide for a desired solubility (and hence concentration) of any pharmaceutical agent or medicinal compound that have increased solubility in light mineral oil as opposed to squalane alone.

The composition can be ophthalmically applied 2-3 times a day or just once at night to deliver sufficient concentrations of a payload pharmaceutical, medicinal herb or other medicament, enabling once daily or possible less frequent dosing and still yield desired treatment of the ophthalmic condition.

The composition can be applied directly to the eyelid margin and still be medically therapeutic. A suitable applicator may be a roller, with an applicator ball or cylinder up to several millimeters in width. Other acceptable applicators are eye droppers which can naturally be used to apply the composition directly to the ocular surface, as well as to an eyelid. An alternate method of application is to apply an aliquot of the composition to a finger, e.g., a drop from an eye dropper, or a half-inch swipe of a roller (depending on the size of the roll surface) and then use the finger to transfer the composition to the eyelid which with proximate natural blinking permits migration of the oil to the eyeball. Aliquots of the composition may be provided in single-use disposable containers, such as bottles or tubes, each containing enough for a single application when needed but not for sterilization purposes.

The composition vehicle can also be used as eye lid skin moisturizer and not be deleterious to the eye itself.

This composition serves as a delivery vehicle for oil-soluble drugs or other oils that are themselves hygroscopic sufficient to be self preserving thus not alter the basic advantages of the composition.

DETAILED DESCRIPTION

The following definitions are used to describe the present invention. In instances where a term is not specifically defined, the definition to be used is that which one of ordinary skill in the art would use to define that term within the context of that term's use.

The term "patient" or "subject" is used to describe an animal, especially a human patient in need, who receives medical attention, care, or treatment of the present invention.

The term "effective" is used to describe an amount of an ophthalmic composition, or a component, extract, material or solvent of a composition which is used to produce an intended effect in amount consistent the effect desired and may vary with the effect desired or which occurs.

The term "mineral oil" or "light mineral oil" is used throughout the specification to describe any of various lubricious, hydrophobic and combustible substances obtained from mineral matter. Mineral oils for use in the present invention may include petroleum-based oil derivatives such as purified petrolatum and mineral oil, particularly light-weight oil, N.F. (national formula). Petroleum-derived oils include aliphatic or wax-based oils, aromatic or asphalt-based oils and mixed base oils. Preferred mineral oils for use in the present invention include petrolatum, mineral oil or mixtures of petrolatum and mineral oil where the amount of petrolatum to mineral oil (on a weight/weight basis) ranges from about 1:20 to about 10:1, preferably about 1:5 to about 5:1, more preferably about 1:3 to about 1:1, depending upon the end use of the emulsion composition.

The compositions of the present invention are preferably hydrophobic and lipophilic. Both squalane and mineral oils as used in the present invention are non-polar oils which are essentially hydrophobic and lipophilic.

Preferably, the pharmaceutical compositions of this invention are administered topically, that is, by direct contact with a patient's eye or a patient's skin surface around an eye, for instance, on an eyelid. The compositions may be applied by brush (generally a single-use application), roller, eye dropper, finger, or pad (single use applications). Alternatively, the compositions may be applied directly to the surface of the eye via an eyedropper or possibly via a spray or jet.

It is contemplated that compositions of the present invention are effectively devoid of water, preservatives, emulsifiers and dispersing agents. The benefit is substantial in reducing undesirable side effects that these agents have. Drug-delivery compositions of the present invention include significant amounts only of squalane, mineral oil and a pharmaceutical compound or medicinal agent that constitutes a therapeutic payload. Any other ingredients are incidental and have no discernable or practical effect on the properties of the composition or its effectiveness in therapeutic application.

Methods for preparing dosage forms are known or will be apparent to those skilled in the art; for example, see "Remington's Pharmaceutical Sciences" (17th Ed., Mack Pub. Co, 1985). The person of ordinary skill will take advantage of favorable pharmacokinetic parameters of the pro-drug forms of the present invention, where applicable, in delivering the present compounds to a patient suffering from an ophthalmic infection to maximize the intended effect of the compound.

In addition to the carrier or delivery vehicle as described herein, a composition for treating one or more disease eye conditions may contain multiple active ingredients or therapeutic agents in the treatment of any one or more of the disease states or conditions. Effective amounts or concentrations of each of the active compounds are to be included within pharmaceutical or therapeutic compositions according to the present invention. Individual therapeutic agents may be administered either sequentially or simultaneously in separate or combined pharmaceutical formulations.

When one or more of the compounds according to the present invention is used in combination with a second therapeutic agent active the dose of each compound may be either the same as or differ from that when the compound is used alone. Appropriate doses will be readily appreciated by those skilled in the art.

In method aspects according to the present invention, one or more compositions according to the present invention may be administered to a patient in the treatment or prevention of any disease state or condition previously mentioned. An effective amount of an therapeutic agent as otherwise described herein is administered to a patient exhibiting symptoms of a disease state or condition as otherwise described herein in order to treat the symptoms of the disease state and/or condition and reduce or eliminate the likelihood that the disease state or condition will escalate or worsen.

Therapeutic ophthalmic compositions according to the present invention comprise an effective amount of one or more of therapeutic agents in liquid, semi-liquid or solid form, otherwise described herein, in combination with the delivery vehicle or petrolatum ointment carrier comprising squalane and optionally mineral oil or mixture of mineral oils. At least one additional agent useful in treating an ophthalmic or other disease state or condition may be included in the composition. In this aspect of the invention, multiple compounds may be advantageously formulated to be coadministered for the prophylactic and/or thereapeutic treatment of any one or more of the disease states or conditions described hereinabove.

The individual components of such combinations as described above may be administered either sequentially or simultaneously in separate or combined pharmaceutical formulations. When one or more compositions according to the present invention are used in combination with a second therapeutic agent, the dose of each may be either the same as or differ from that when the compound is used alone. Appropriate doses will be readily appreciated by those skilled in the art.

EXAMPLES

An ophthalmic treatment composition for the treatment of dry eye consists essentially of squalane in an amount by weight of 1% to 99%; and mineral oil in an amount by weight of 1% to 99%. Preferably, the mineral oil is a light mineral oil or mixture of light mineral oils and is present in an amount by weight of 1% to 10%. The composition is effectively devoid of water, preservatives, emulsifiers and dispersing agents. Thus, any trace amounts of such substances are negligible in terms of effects on properties of the composition and effects on mammalian subjects.

A related method for treating keratoconjunctivitis sicca in a mammal in need thereof consists of administering to the mammal in need thereof therapeutically effective amounts of a composition comprising 100% squalane or optionally squalane in combination with a mineral oil or mixture of mineral oils. The composition comprises squalane in an amount by weight of 1% to 100%, and mineral oil in an amount by weight of 0% to 99%. The method of administering of the composition preferably comprises topically applying a therapeutically effective amount thereof to an eye or eyelid of the mammal. The composition may be applied one to three or four times daily. The application may be effect either on mammalian subjects to which the composition is applied or on the properties of the composition including its storage stability, anticontaminant attributes that preclude need for preservatives.

A method for treating an ophthalmic disease state or condition in a mammal in need thereof consists of administering to the mammal in need thereof therapeutically effective amounts of a composition comprising squalane in combination with a hydrophobic pharmaceutical substance in an amount by weight of 0.01% to 5% and optionally mineral oil or a mixture of mineral oils in an amount sufficient to solubilize the hydrophobic pharmaceutical substance.

As indicated above, the pharmaceutical substance may be cyclosporin, hydrocortisone, prednisone, or prednisolone in an amount by weight of 0.5%-2%, a hydrophobic antibiotic, a hydrophobic anti-inflammatory, an hydrophobic antihistamine, a hydrophobic NSAID, or a hydrophobic hormone or any mixture of these substances.

In the examples below, the mineral oil is typically light mineral oil, N.F.

Dry Eye Treatment Compositions and Methods
Symptoms: dry eye
Composition: 90% squalane, 10% mineral oil
Administration: 3-5 drops daily, preferably all together in the evening before bedtime
Symptoms: dry eye
Composition: 95% squalane, 5% mineral oil
Administration: 3-5 drops daily, preferably all together in the evening before bedtime
Symptoms: dry eye
Composition: 80% squalane, 20% mineral oil
Administration: 3-5 drops daily, preferably all together in the evening before bedtime
Symptoms: dry eye
Composition: 90% squalane, 10% mineral oil
Administration: 1-3 drops, 3 times daily
Symptoms: dry eye
Composition: 95% squalane, 5% mineral oil
Administration: 1-3 drops, 3 times daily
Symptoms: dry eye
Composition: 80% squalane, 20% mineral oil
Administration: 1-3 drops, 3 times daily
Symptoms: dry eye
Composition: 60% squalane, 40% mineral oil
Administration: 1-3 drops, 3 times daily
Symptoms: dry eye
Composition: 20% squalane, 80% mineral oil Administration: 3-5 drops daily, preferably all together in the evening before bedtime
Symptoms: dry eye
Composition: 5% squalane, 95% mineral oil
Administration: 3-5 drops daily, preferably all together in the evening before bedtime
Symptoms: dry eye
Composition: 55% squalane, 45% mineral oil
Administration: 3-5 drops daily, preferably all together in the evening before bedtime
Symptoms: dry eye
Composition: 10% squalane, 80% mineral oil
Administration: 3-5 drops daily, preferably all together in the evening before bedtime
Symptoms: dry eye
Composition: 40% squalane, 20% mineral oil
Administration: 3-5 drops daily, preferably all together in the evening before bedtime
Symptoms: dry eye
Composition: 55% squalane
Administration: 3-5 drops daily, preferably all together in the evening before bedtime
Symptoms: dry eye
Composition: 55% squalane, 25% mineral oil
Administration: 3-5 drops daily, preferably all together in the evening before bedtime
Symptoms: dry eye
Composition: 5% squalane, 95% mineral oil
Administration: 1-3 drops, 3 times daily
Symptoms: dry eye
Composition: 55% squalane, 45% mineral oil
Administration: 1-3 drops, 3 times daily
Symptoms: dry eye
Composition: 10% squalane, 90% mineral oil
Administration: 1-3 drops, 3 times daily
Symptoms: dry eye
Composition: 40% squalane, 60% mineral oil
Administration: 1-3 drops, 3 times daily
Symptoms: dry eye
Composition: 90% squalane, 9% mineral oil, 1% cyclosporin
Administration: 3-5 drops daily, preferably all together in the evening before bedtime
Symptoms: dry eye
Composition: 94% squalane, 5% mineral oil, 1% cyclosporin
Administration: 3-5 drops daily, preferably all together in the evening before bedtime
Symptoms: dry eye
Composition: 93% squalane, 5% mineral oil, 2% cyclosporin
Administration: 3-5 drops daily, preferably all together in the evening before bedtime
Symptoms: dry eye
Composition: 80% squalane, 18% mineral oil, 2% cyclosporin
Administration: 3-5 drops daily, preferably all together in the evening before bedtime
Symptoms: dry eye
Composition: 78% squalane, 18% mineral oil, 4% cyclosporin
Administration: 3-5 drops daily, preferably all together in the evening before bedtime
Symptoms: dry eye
Composition: 70% squalane, 27% mineral oil, 3% cyclosporin
Administration: 3-5 drops daily, preferably all together in the evening before bedtime
Symptoms: dry eye
Composition: 88% squalane, 10% mineral oil, 2% cyclosporin
Administration: 1-3 drops, 3 times daily
Symptoms: dry eye
Composition: 92% squalane, 5% mineral oil, 3% cyclosporin
Administration: 1-3 drops, 3 times daily
Symptoms: dry eye
Composition: 80% squalane, 16% mineral oil, 4% cyclosporin
Administration: 1-3 drops, 3 times daily
Symptoms: dry eye
Composition: 80% squalane, 19% mineral oil, 1% cyclosporin
Administration: 1-3 drops, 3 times daily
Symptoms: dry eye
Composition: 50% squalane, 49% mineral oil, 1% cyclosporin
Administration: 3-5 drops daily, preferably all together in the evening before bedtime
Symptoms: dry eye
Composition: 60% squalane, 38% mineral oil, 2% cyclosporin
Administration: 3-5 drops daily, preferably all together in the evening before bedtime
Symptoms: dry eye
Composition: 75% squalane, 23% mineral oil, 2% cyclosporin
Administration: 3-5 drops daily, preferably all together in the evening before bedtime
Symptoms: dry eye
Composition: 18% squalane, 80% mineral oil, 2% cyclosporin
Administration: 3-5 drops daily, preferably all together in the evening before bedtime
Symptoms: dry eye
Composition: 40% squalane, 59% mineral oil, 1% cyclosporin
Administration: 3-5 drops daily, preferably all together in the evening before bedtime
Symptoms: dry eye
Composition: 55% squalane, 42% mineral oil, 3% cyclosporin
Administration: 3-5 drops daily, preferably all together in the evening before bedtime
Symptoms: dry eye
Composition: 50% squalane, 49% mineral oil, 1% cyclosporin
Administration: 1-3 drops, 3 times daily
Symptoms: dry eye
Composition: 50% squalane, 46% mineral oil, 4% cyclosporin
Administration: 1-3 drops, 3 times daily
Symptoms: dry eye
Composition: 55% squalane, 43% mineral oil, 2% cyclosporin
Administration: 1-3 drops, 3 times daily
Symptoms: dry eye
Composition: 10% squalane, 88% mineral oil, 2% cyclosporin
Administration: 1-3 drops, 3 times daily
Symptoms: dry eye
Composition: 40% squalane, 59% mineral oil, 1% cyclosporin Administration: 1-3 drops, 3 times daily
Symptoms: dry eye
Composition: 55% squalane, 44% mineral oil, 1% cyclosporin
Administration: 1-3 drops, 3 times daily
Symptoms: dry eye
Composition: 55% squalane, 43% mineral oil, 2% cyclosporin
Administration: 1-3 drops, 3 times daily Hydrocortisone Hydrocortisone or hydrocortisone acetate belongs to a group of medicines called corticosteroids and is used to relieve redness and swelling, to treat non-infected conditions such as swelling of parts of the eye and injury to the cornea. In addition, hydrocortisone is used to treat viral infection (by herpes zoster) of the eye. Dosage schedule is exemplarily 3-5 drops at bedtime daily, or 1-3 drops three times daily, until symptoms dissipate.

TABLE 1

Hydrocortisone

| Example No. | Squalane | Mineral Oil | Hydrocortisone |
|---|---|---|---|
| 1 | 98% | 1.99% | 0.01% |
| 2 | 90% | 9.99% | 0.01% |
| 3 | 98% | 1.9% | 0.1% |
| 4 | 95% | 4.9% | 0.1% |
| 5 | 90% | 9.9% | 0.1% |
| 6 | 98% | 1.5% | 0.5% |
| 7 | 95% | 4.5% | 0.5% |
| 8 | 90% | 9.5% | 0.5% |
| 9 | 97% | 2% | 1% |
| 10 | 95% | 4% | 1% |
| 11 | 90% | 9% | 1% |
| 12 | 95% | 3% | 2% |
| 13 | 90% | 8% | 2% |
| 14 | 85% | 13% | 2% |

Prednisone and Prednisolone

Prednisone may be used to treat ocular inflammation. Ophthalmic prednisolone reduces the irritation, redness, burning, and swelling of eye inflammation caused by chemicals, heat, radiation, infection, allergy, or foreign bodies in the eye. It sometimes is used after eye surgery. Dosage schedule is exemplarily 3-5 drops daily, or 1-3 drops three times daily, until symptoms dissipate.

TABLE 2

Prednisone or Prednisolone

| Example No. | Squalane | Mineral Oil | Prednisone or prednisolone |
|---|---|---|---|
| 1 | 98% | 1.99% | 0.01% |
| 2 | 90% | 9.99% | 0.01% |
| 3 | 98% | 1.9% | 0.1% |
| 4 | 95% | 4.9% | 0.1% |
| 5 | 90% | 9.9% | 0.1% |
| 6 | 98% | 1.5% | 0.5% |
| 7 | 95% | 4.5% | 0.5% |
| 8 | 90% | 9.5% | 0.5% |
| 9 | 97% | 2% | 1% |
| 10 | 95% | 4% | 1% |
| 11 | 90% | 9% | 1% |
| 12 | 95% | 3% | 2% |
| 13 | 90% | 8% | 2% |
| 14 | 85% | 13% | 2% |

Antiobiotics

Erythromycin is an antibiotic commonly prescribed for treating conjunctivitis. Ciprofloxacin is an antibiotic commonly prescribed for treating keratitis caused by two of the most clinically significant forms of ocular bacteria, *S. aureus* and *P. aeruginosa*. Dosage schedule is exemplarily 3-5 drops daily, evenly spaced depending on severity until symptoms dissipate or altered by a physician.

TABLE 3

Erythromycin or ciprofloxacin

| Example No. | Squalane | Mineral Oil | Erythromycin; ciprofloxacin |
|---|---|---|---|
| 1 | 98% | 1.99% | 0.01% |
| 2 | 90% | 9.99% | 0.01% |
| 3 | 98% | 1.9% | 0.1% |
| 4 | 95% | 4.9% | 0.1% |
| 5 | 90% | 9.9% | 0.1% |
| 6 | 98% | 1.5% | 0.5% |
| 7 | 95% | 4.5% | 0.5% |
| 8 | 90% | 9.5% | 0.5% |
| 9 | 97% | 2% | 1% |
| 10 | 95% | 4% | 1% |
| 11 | 90% | 9% | 1% |
| 12 | 95% | 3% | 2% |
| 13 | 90% | 8% | 2% |
| 14 | 85% | 13% | 2% |

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for treating dry eye in a mammal in need thereof consisting of administering to an eye or surrounding tissues of said mammal in need thereof a therapeutically effective amount of composition comprising squalane in an amount of at least 80% volume/volume of the composition, wherein the squalane inhibits dry eye, and a pharmaceutical substance in an amount by weight of 0.01% to 5% of the weight of the entire composition, the composition being effectively devoid of water, preservatives, emulsifiers and dispersing agents.

2. The method defined in claim 1 wherein said pharmaceutical substance is taken from the group consisting of hydrocortisone, prednisone, and prednisolone in an amount by weight of 0.5%-2% of the weight of the entire composition.

3. The method defined in claim 1 wherein said pharmaceutical substance is taken from the group consisting of a hydrophobic antibiotic, a hydrophobic anti-inflammatory, an hydrophobic antihistamine, a hydrophobic NSAID, and a hydrophobic hormone.

4. The method defined in claim 1 wherein the administering of said composition includes applying said composition to an eye or eyelid of said mammal.

5. The method defined in claim 1 wherein the administering of said composition includes using an applicator taken from the group consisting of a roller, an eye dropper, a pad, and a brush.

6. The method defined in claim 1 wherein the pharmaceutical substance is hydrophobic and the composition includes mineral oil or a mixture of mineral oils in an amount of 1% to 10% volume/volume of the composition.

7. The method defined in claim 6 wherein said pharmaceutical substance is cyclosporin.

8. The method defined in claim 1 wherein the composition includes squalane in an amount of at least 90% volume/volume.

9. A method for treating dry eye in a mammal in need thereof consisting of administering to an eye or surrounding tissues of said mammal in need thereof a therapeutically effective amount of a composition comprising:
   squalane in an amount of at least 80% volume/volume of the composition, wherein the squalane inhibits dry eye;
   a hydrophobic pharmaceutical substance in an amount by weight of 0.01% to 5% of the weight of the entire composition; and
   mineral oil or a mixture of mineral oils in an amount of 1% to 10% volume/volume of the composition,
   the composition being effectively devoid of water, preservatives, emulsifiers and dispersing agents.

10. The method defined in claim 9 wherein the composition includes squalane in an amount of at least 90% volume/volume.

11. The method defined in claim 10 wherein the mineral oil or mixture of mineral oils is present in an amount of 1% to 5% volume/volume of the composition.

12. A method for treating an ophthalmic disease state or condition in a mammal in need thereof and for inhibiting dry eye, wherein the ophthalmic condition or state is taken from the group consisting of redness and swelling; injury to the cornea; viral infection by herpes zoster of the eye; irritation, redness, burning, and swelling of eye inflammation caused by chemicals, heat, radiation, infection, allergy, or foreign bodies in the eye; conjunctivitis; and keratitis caused by the ocular bacteria *S. aureus* and *P. aeruginosa*, the method consisting of administering to an eye or surrounding tissues of said mammal in need thereof a therapeutically effective amount of a composition comprising:
   squalane in an amount of at least 80% volume/volume of the composition, wherein the squalane inhibits dry eye;
   a pharmaceutical substance in an amount by weight of 0.01% to 5% of the weight of the entire composition,
   the composition being effectively devoid of water, preservatives, emulsifiers and dispersing agents.

13. The method defined in claim 12, wherein said pharmaceutical substance is taken from the group consisting of cyclosporin, hydrocortisone, prednisone, prednisolone, a hydrophobic antibiotic, a hydrophobic anti-inflammatory, an hydrophobic antihistamine, a hydrophobic NSAID, and a hydrophobic hormone.

\* \* \* \* \*